United States Patent [19]

Moran et al.

[11] Patent Number: 5,697,935

[45] Date of Patent: Dec. 16, 1997

[54] DEVICE AND METHOD FOR REMOVING FASTENING IMPLEMENTS FROM BONE

[75] Inventors: Ronald D. Moran, Yucaipa; G. Allen Gustafson, Redlands, both of Calif.

[73] Assignee: Medex Marketing, Inc., Billerica, Mass.

[21] Appl. No.: 527,673

[22] Filed: Sep. 12, 1995

[51] Int. Cl.[6] ............................................. A61B 17/88
[52] U.S. Cl. ........................... 606/104; 606/80; 606/86; 408/201; 408/703
[58] Field of Search .......................... 606/104, 86, 96, 606/179, 80, 79; 408/204, 703

[56] References Cited

U.S. PATENT DOCUMENTS

| 4,573,838 | 3/1986 | Omi et al. ........................ 408/204 |
| 4,767,244 | 8/1988 | Peterson ........................... 408/204 |

FOREIGN PATENT DOCUMENTS

| A9201046 | 1/1994 | Netherlands . |
| A1022328 | 3/1966 | United Kingdom . |
| A1601591 | 11/1981 | United Kingdom . |
| A9106261 | 5/1991 | WIPO . |

OTHER PUBLICATIONS

AESCULAP: "Instrumentarium zur Entfernung abgebrochener Osteosythesechrauben" Sep. 1985 XP002020414 * p. 3, bottom section; p. 3, top section, Extraktionshulse, mit innenliegendem . . ..

Primary Examiner—Michael Buiz
Assistant Examiner—Daphna Shai
Attorney, Agent, or Firm—Dority & Manning

[57] ABSTRACT

A device for removing embedded or broken fastening implements from bone, comprises a cylindrical drill bit with a cavity extending internally from a distal end of the bit. The distal end further defines a cutting surface disposed about the opening to the cavity. The interior surface of the cavity defines has a decreasing diameter as one proceeds away from the opening in the distal end, and thus the cutting surface is formed where the radial thickness of the wall of the drill bit is the thinnest. The interior surface of the cavity is susceptible to a galling effect when frictionally engaged by the exterior surface of the fastening implement intended to be removed. The operator places the drill bit around the site of the bone containing the fastening implement to be removed and rotates the bit so as to cut into the bone around the exterior surface of the fastening implement. Galling between the interior surface of the cavity and the exterior surface of the fastening implement causes the implement to adhere to the interior surface of the cavity of the drill bit. The operator then can move the drill bit away from the bone and remove the adhered fastening implement, which then can be discarded with the drill bit.

15 Claims, 2 Drawing Sheets

DEVICE AND METHOD FOR REMOVING FASTENING IMPLEMENTS FROM BONE

BACKGROUND OF THE INVENTION

The present invention relates to apparatus and method for extracting screws and pins from bone.

The use of fastening implements, such as stainless steel pins and screws, in the treatment of bone fractures is known and has become widespread. Screws used in the treatment of bone fractures typically have a head portion that is configured to receive a tool used to introduce the screw into the bone and remove the screw when the healing process has sufficiently advanced to permit such removal of the screw. However, the head of the screw can become detached from the screw or so damaged as to preclude use of the tool to remove the screw. Some types of pins, such as Haggi pins, are intended to remain permanently in the bone as part of the treatment. However, it occasionally occurs that such a permanent pin needs to be removed. Because of the intended permanent disposition of the Haggi pin in the bone, such Haggi pins typically are configured so that the portion of the pin near the surface of the bone does not contain any features that enable the pin to be extracted readily from the bone.

A significant clinical problem can arise with buried pins, broken screws or fragments thereof that cannot be removed from bone. This often poses a problem concerning the hip joint. For example, after a failed hip arthroplasty, especially revision arthroplasty, pins may become buried in the femoral head, or broken screws may become buried in the acetabulum. One method of removing such pins and screws is to use a coring device that fits over the entire length of the pin or screw and removes the pin or screw together with the surrounding core sample of the bone. However, this method results in the removal of a significant amount of bone. Moreover, as the coring device probes deeper into the bone, the danger posed by this method to the vascular structures of the bone becomes greater. Another method uses a coring device to expose the end of the buried pin or screw, and uses jaws to grip the end so that the screw or pin can be yanked out of the bone. However, this method does significant damage to the bone surrounding the buried screw or pin.

Thus, removal of such pins and screws becomes a difficult and time-consuming surgical undertaking. Moreover, the risks associated with such difficult surgery can eliminate removal of the pin or screw as an option to a treatment regimen that otherwise would be desired by the treating physician. The difficulty in removing such pins and screws can result in a set back and/or delay in the recovery of the patient.

OBJECTS AND SUMMARY OF THE INVENTION

It is a principal object of the present invention to provide an improved device and method for the removal of fastening implements such as buried pins, permanent pins, headless screws, and damaged screws and pins used in the treatment of various bone fractures and other bone treatments.

It is another principal object of the present invention to provide a device and method for grabbing the tip of a fastening implement such as a screw or pin embedded in bone such that bone destruction is reduced in comparison to current devices and methods.

It is a further principal object of the present invention to provide a device and method for grabbing the tip of a fastening implement such as a screw or pin embedded in bone such that the time needed to perform the procedure is reduced in comparison to current devices and methods.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described in summary fashion herein, the device of the present invention for removing embedded or broken fastening implements from bone, comprises a cylindrical drill bit. The cylindrical drill bit includes an elongated cylindrical member that defines a proximal end and a distal end disposed generally opposite from the proximal end. The cylindrical member defines a cavity disposed internally of the cylindrical member and has a central axis extending along the length of the cylindrical member. The distal end defines an opening concentrically disposed with respect to the cavity and communicating with the cavity. The distal end further defines at least one cutting surface disposed about the opening. The cavity defines an interior surface having a decreasing diameter as one proceeds from the distal end to the proximal end. In the region of the distal end containing the cutting surface and the cavity in a preferred embodiment, the exterior surface of the cylindrical member has a uniform diameter. Accordingly, the cutting surface is formed where the radial thickness of the wall of the cylindrical member is the thinnest. Where the fastening implements to be removed are formed of stainless steel, the cylindrical member is desirably composed of stainless steel. Only the portion of the cylindrical member containing the cutting surface is hardened, thereby leaving the interior surface of the cavity susceptible to a galling effect when frictionally engaged by the exterior surface of the fastening implement intended to be removed.

According to the method for removing from bone, fastening implements such as bone pins and headless bone screws, embedded in the bone, a cylindrical drill bit having an opening configured to receive the end of the fastening implement therein and having a cavity configured with a decreasing diameter as one proceeds deeper into the cavity, is disposed by the operator concentrically around the site of the bone containing the fastening implement to be removed. The diameter of the opening in the distal end of the cylindrical drill bit is chosen so that it is as close as possible to the diameter of the screw or pin to be removed. The operator rotates the cylindrical bit so as to cut into the bone around the exterior surface of the fastening implement. The operator rotates the drill bit at least until galling between the interior surface of the cavity and the exterior surface of the fastening implement causes the implement to adhere to the interior surface of the cavity of the drill bit. If a threaded screw is being removed, then the operator will rotate the drill bit in the direction that unscrews the screw. Thus, when the screw becomes fixed to the drill bit, the screw will begin unscrewing and move away from and out of the bone. If an unthreaded pin is being removed, once the pin becomes fixed to the interior surface of the cavity in the drill bit, the operator then can move the cylindrical drill bit away from the bone and remove the adhered pin. The removed fastening implement, be it pin or screw, then can be discarded together with the drill bit to which the implement has become adhered.

The accompanying drawings, which are incorporated in and constitute a part of this specification, illustrate one embodiment of the invention and, together with the description, serve to explain the principles of the invention.

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. The same numerals are assigned to the same components throughout the drawings and description.

Figure 1:
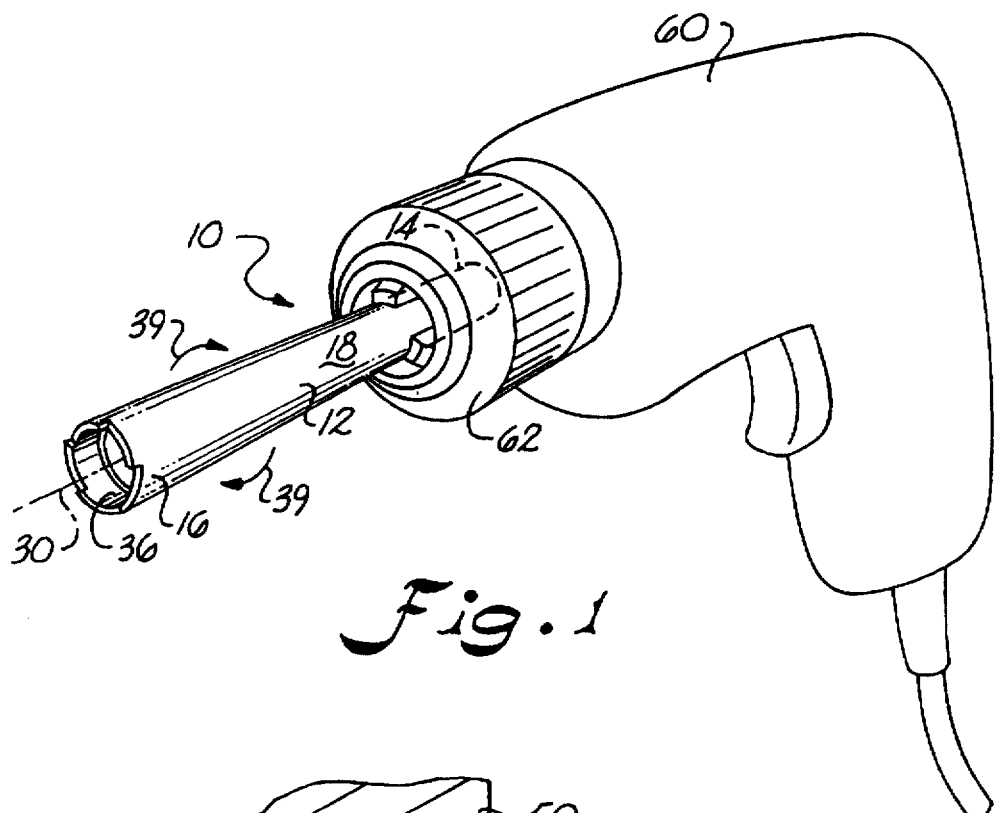
FIG. 1 is an elevated perspective view of a preferred embodiment of the present invention.
Figure 2:
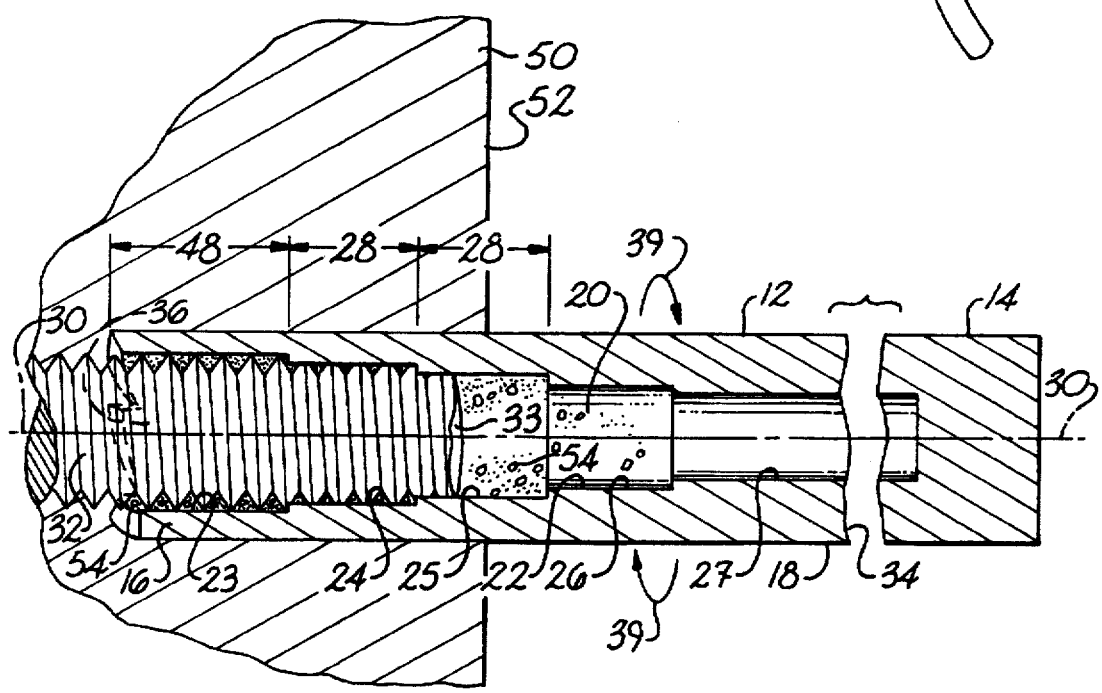
FIG. 2 is a cross-sectional view of a preferred embodiment of the present invention in operation to remove a headless bone screw from bone.
Figure 3:
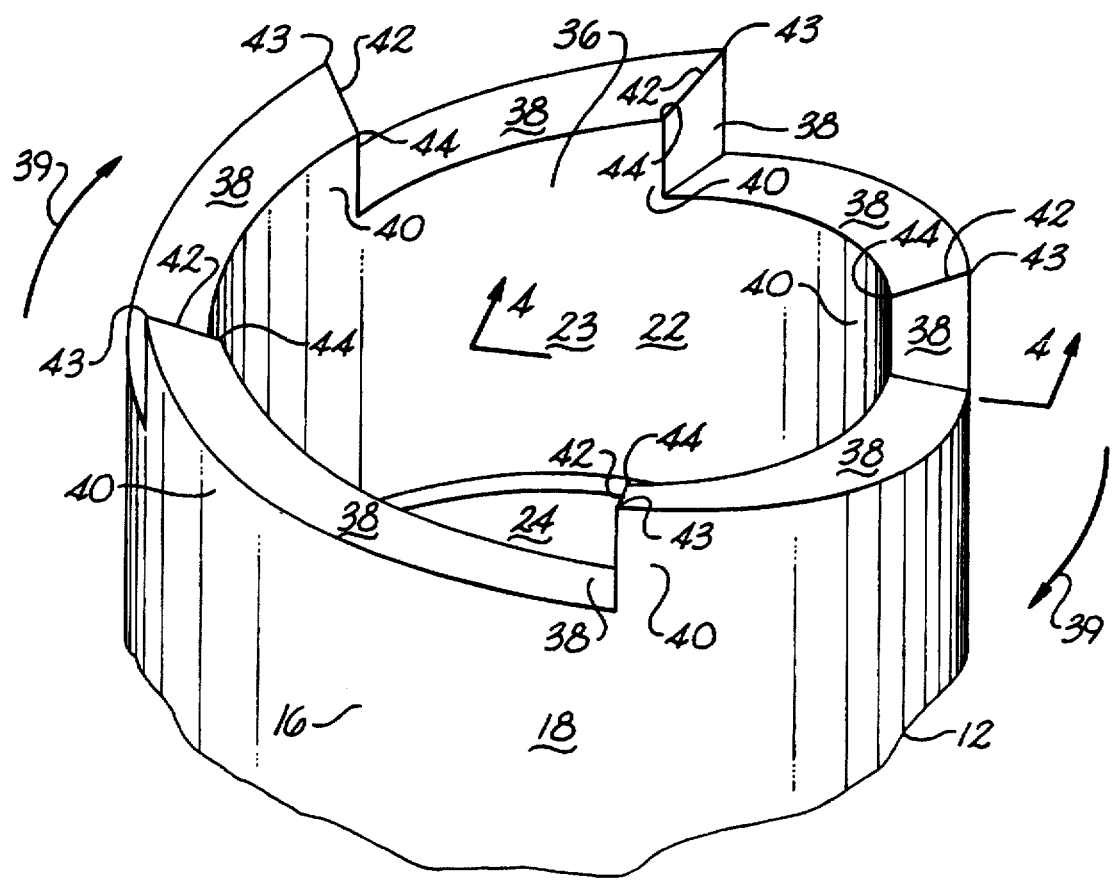
FIG. 3 is a detailed partial elevated perspective view of the embodiment of the present invention shown in FIGS. 1 and 2.

A presently preferred embodiment of the present invention is shown in FIG. 1 and is represented generally by the numeral 10. As shown in FIGS. 1 and 2, the device of the present invention includes a cylindrical drill bit in the form of an elongated cylindrical member 12 defining a proximal end 14 and a distal end 16 disposed generally opposite from proximal end 14. As shown in FIGS. 1-3, elongated cylindrical member 12 is configured with an exterior surface 18 having a substantially uniform diameter along the entire length thereof. However, in an alternative embodiment (not shown) the exterior surface 18 of the distal end 16 of elongated member 12 can be provided with a different diameter than the exterior surface of the proximal end. As designated generally by the numeral 20 in FIG. 2, elongated cylindrical member 12 is configured with an elongated cavity, which occupies a portion of the length of distal end 16 of elongated member 12. As shown in FIG. 2, cavity 20 is defined by an interior surface 22, and the diameter of cavity 20 and interior surface 22 decreases as one proceeds from distal end 16 to proximal end 14.

In a presently preferred embodiment shown in FIG. 2 for example, interior surface 22 of cavity 20 is defined by at least two adjacent and concentric sections 23, 24. As shown in FIG. 2, a plurality of adjacent sections 23, 24, 25, 26, 27 can be provided, and the diameter of each section 23, 24, 25, 26, 27 becomes progressively smaller in steps as one proceeds from the distal end 16 of cylindrical member 12 toward proximal end 14 of cylindrical member 12. As a rule-of-thumb, the difference in diameter between adjacent sections of the interior surface 22 of cylindrical member 12 is desirably one half millimeter. Moreover, as between two adjacent sections such as section 23 and section 24, the section disposed closer to distal end 16, in this case section 23, is defined by the larger diameter of each two adjacent sections. In addition, as another rule-of-thumb and as shown in FIG. 2, a desirable nominal dimension for the axial depth 28 of each section 24, 25 measured along the central axis 30 of cavity 20 is approximately 75% of the diameter of the screw 32 being removed.

The structural portion of elongated cylindrical member between interior surface and exterior surface (with its constant diameter) toward distal end defines the wall 34 of elongated cylindrical member. In the embodiment shown in FIG. 2 for example, the radial thickness of wall 34 varies in steps as one proceeds from distal end 16 to proximal end 14. Accordingly, the diameter of interior surface 22 also varies in steps as one proceeds from distal end 16 to proximal end 14. However, in an alternative embodiment of elongated cylindrical member 12, the variation of the radial thickness of wall 34 and the diameter of cavity 20 could be made linear, as in a cone-shaped cavity, rather than "stepped" (as shown in FIG. 2). As a rule-of-thumb, the radial thickness of wall 34 near opening 36 of elongated member 12 is such that the diameter of exterior surface 18 at distal end 16 of elongated cylindrical member 12 is approximately one millimeter larger than the inside diameter of cavity 20 near opening 36. This reduces the amount of bone material that is removed during the method of using the cylindrical drill bit of the present invention.

As generally designated by the numeral 36 in FIGS. 1-3, an opening is defined at the leading edge or free end of distal end 16, and opening 36 forms the mouth or entrance of cavity 20. As shown in FIGS. 1 and 2, opening 36 has a central axis 30 extending along the length of cylindrical member 12. Elongated cavity 20 extends axially from opening 36 toward proximal end 14 and is disposed concentrically relative to opening 36, which communicates directly with cavity 20.

Figure 4:
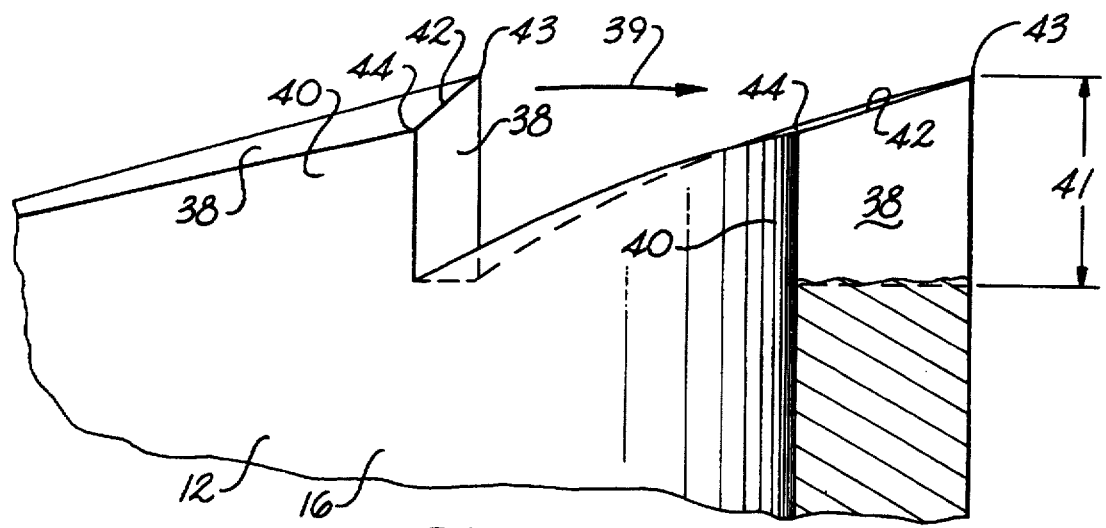
FIG. 4 is a partial cross-sectional view taken in the direction in which arrows 4—4 point in FIG. 3.

In accordance with the present invention, the free edge of the distal end of the cylindrical member defines at least one leading edge that forms a cutting surface for the drill bit of the present invention. As shown in FIGS. 3 and 4 for example, the free edge 38 of distal end 16 of the cylindrical member 12 of the cylindrical drill bit of the present invention, defines at least one cutting surface. As shown in FIGS. 1-4, the leading edge of distal end 16 is provided with a plurality of generally triangular-shaped teeth. As shown in FIGS. 3 and 4, each triangular tooth 40 is provided with a free edge 42 that forms part of the leading edge of distal end 16 of cylindrical member 12 and serves as a cutting edge 42. The cutting surface of the cylindrical drill bit is desirably formed by the cutting edge 42 of each tooth 40. As shown in FIGS. 1 and 3 for example, each cutting edge 42 of each tooth 40 is disposed about opening 36, and thus the cutting surface of the cylindrical drill bit of the present invention is disposed about opening 36. As shown in FIG. 3 for example, the cutting surface is configured to cut when the cutting surface is rotated about central axis 30 of opening 36 in a direction that is the direction for unscrewing the bone screw 32 (FIG. 2) that is intended to be removed. As shown in FIG. 3, this removal direction would be the counter clockwise direction from the perspective of one looking directly at FIG. 3. This direction for unscrewing the bone screw intended to be removed is indicated generally by the arrows designated 39 in FIGS. 1-4 for example.

In accordance with the present invention, the cutting surface is configured to move debris toward the central axis 30 of opening 36. As shown in FIGS. 3 and 4 for example, each cutting edge 42 of each tooth 40 defines a relatively high point 43 at exterior surface 18 of cylindrical member 12 and a relatively low point 44 at interior surface 22 of cylindrical member 12. Moreover, as one moves each cutting edge 42 during the cutting motion, high point 43 is relatively forward, i.e., advanced, relative to low point 44. In a typical disposition of cutting edge 42, cutting edge 42 would extend at an angle of something in the range of from 20 to 25 degrees from a radius drawn to high point 43. As a result of this configuration, each cutting edge 42 is angled toward the central axis 30 of opening 36. In this way, as each cutting edge 42 of the cutting surface performs its cutting function during rotation of cylindrical member 12, the debris composed of the bone fragments removed by the cutting edge 42 is pushed toward central axis 30 of opening 36 by the biased surface 42 constituting the cutting edge.

As shown in FIG. 3, the cutting surface defines at least a first tooth 40, a second tooth 40, and a third tooth 40. The high point 43 of each tooth 40 is separated circumferrentially from the high point 43 or vertex of each other tooth 40. The circumferrential separation between the vertex 43 of first tooth 40 and the vertex 43 of second tooth 40 differs from the circumferrential separation between the vertex 43 of second tooth 40 and the vertex 43 of third tooth 40. Thus, the circumferential distance between the high points 43 of the teeth 40 are desirably varied as between adjacent teeth 40. In other words, the pitch between adjacent teeth 40 varies. In this way, the high points 43 will not touch symmetrically on the surface of the bone 50 as the cutting surface of the cylindrical drill bit is rotated.

As a rule-of-thumb and as shown in FIG. 4, the height dimension (indicated by the designating numeral 41) of each tooth 40 desirably is on the order of 1 to 1.5 millimeters in the case of a device for removing screws and pins of typical diameters found in orthopaedic procedures performed on human beings. Moreover, as another useful rule-of-thumb and shown in FIG. 2 for example, the axial distance 48 measured between the high points 43 of teeth 40 of the cutting surface and the beginning of the second section 24 (assuming the first section 23 includes teeth 40) is approximately the diameter of the screw 32 that is intended to be removed. In a presently preferred embodiment, the teeth are desirably heat treated to obtain a 30 to 40 Rockwell hardness result. In a presently preferred embodiment, only the first 3 or 4 millimeters of the distal end of cylindrical member is subjected to the heat treatment that results in the hardening of this portion containing the teeth of the cylindrical drill bit of the present invention. Typically, after cavity 20 is drilled and teeth 40 are cut, the heat treatment of teeth 40 will be performed to harden teeth 40 before the teeth are sharpened.

Elongated cylindrical member desirably is formed of an alloy of stainless steel such as ASTM type 410 or ASTM type 416. The 300 series of ASTM type stainless steel alloy is less desirable if heat treatment of the cutting surfaces is to be performed because the 300 series is believed not to heat treat very well.

As shown in FIG. 2 for example, opening 36 has a diameter that is larger than the largest diameter of the screw or pin 32 that is intended to be removed. Thus, as a useful rule-of-thumb, the radial thickness of wall 34 near opening 36 is desirably less than 1 millimeter. This reduced radial wall thickness at the cutting edge 42 tends to reduce the pressure that must be applied to the cutting surface. Indeed, based on testing done to date, applicants believe that the thrust force and torque that is applied to insert the cortical and cancellous bone screws in human femurs and pelvis, is greater than the pressure and torque required to remove such screws 32 using the cylindrical drill bit device of the present invention. Moreover, the reduced radial wall thickness at the cutting edge 42 tends to reduce the amount of bone removed at the cutting site on the bone 50. Because the radial thickness of wall 34 increases as one proceeds away from the relatively thin section 23 in which cutting edge 42 is formed, cylindrical drill bit 12 has sufficient strength to perform its drilling function, even though the cutting surface is relatively thin.

In accordance with a preferred embodiment of the present invention, at least one of the sections 23, 24, 25, 26, 27 of cylindrical member 12 is sized with a diameter such that as the cutting surface is rotated about central axis 30 of opening 36, this one section 23, 24, 25, 26 or 27 becomes adhered to the exterior surface of the screw 32 that is intended to be removed. This occurs because typically the screw or pin 32 that is intended to be removed is composed of stainless steel material. The interior surface 22 of the section 23, 24, 25, 26 or 27 of the removal device also is composed of stainless steel material, and the friction between the stainless steel surface of the screw or pin and the interior surface 22 of the cylindrical member 12 results in a galling effect that causes a bond to be formed between the exterior surface of the screw or pin 32 and the adjacent surface 22 of the section 23, 24, 25, 26 or 27 of the removal device. Once this bond is formed, the screw or pin 32 tends to rotate together with the cylindrical member 12 of the removal device. Accordingly, rotation of the removal device in the counter clockwise direction, which is the direction in which the screw 32 becomes unscrewed, results in rotation of the screw 32 in the direction in which it becomes unscrewed and loosened for ease of removal. Further rotation of cylindrical member 12 causes the screw 32 to push out of the bone 50.

As shown in FIGS. 1 and 2, the removal device of the present invention can include a mechanism for gripping the cylindrical member and rotating the cylindrical member about the central axis of the opening. As embodied herein and shown in FIG. 1, this mechanism can include a powered, hand-held motor driven mechanism for rotating elongated member in a direction that is the direction in which the screw that is desired to be removed, becomes unscrewed. As shown in FIG. 1, this gripping mechanism can include a drill 60 provided with a chuck 62. Moreover, the drill 60 can be powered by an electric motor or a pneumatic motor, as desired. Typically, a power drill driven by an electric motor can be used. The speed of rotation of the cylindrical member 12 is desirably in a range of 200 to 500 revolutions per minute. However, much slower rotational speeds such as 5 revolutions per minute, can be used so that the rotation of cylindrical member 12 can be effected by manual means. However, it is preferred to rotate cylindrical member 12 in the nominal range of 200 to 500 revolutions per minute.

In operation, a cylindrical drill bit in accordance with the present invention is selected with a configuration suited for a definite diameter, length, and material type of screw or pin 32 that is to be removed. The cavity 20 of the cylindrical drill bit 12 is selected to have an opening 36 that is sized to receive the end 33 of the pin or screw 32 that is near the surface 52 of the bone 50 in question. For example, to remove a typical screw with a diameter in the range 4.2 to 4.5 millimeters, suitable dimensions for a cylindrical drill bit 12 would include an outside diameter of 0.2187 inches (7/32"), an inside diameter of 4.5 mm for section 23, a 4 mm axial depth (48 or 28 in FIG. 2) for each of sections 23, 24, 25, 26 and 27, a 6 cm axial length from distal end 16 to proximal end 14, and respective inside diameters for each section 24, 25, 26, and 27 of 0.166 inches, 0.152 inches, 0.136 inches, and 0.116 inches. Similarly, to remove a typical 6.5 millimeter diameter screw, suitable dimensions for a cylindrical drill bit 12 would include an outside diameter of 7.5 millimeters, an inside diameter of 0.257 inches for section 23, a 5 mm axial depth (48 or 28 in FIG. 2) for each of sections 23, 24, 25, 26 and 27, a 6 cm axial length from distal end 16 to proximal end 14, and respective inside diameters for each section 24, 25, 26, and 27 of 0.234 inches, 0.221 inches, 0.209 inches, and 0.201 inches. Moreover, the axial length can be larger than 6 cm for applications such as would require an angled driver like that available from DuPuy of Warsaw, Ind.

The proximal end 14 of such drill bit 12 is inserted into the end of a chuck 62 of a powered drill 60 as shown in FIG. 1 for example. The operator disposes the distal end 16 of the drill bit 12 with the cutting surface concentrically around the exposed exterior surface of the pin or screw 32 to be removed or around the opening in the bone 50 in which the screw or pin 32 is embedded. This only can occur after the exterior flesh (not shown in FIG. 2) surrounding the bone 50 is parted by a conventional surgical procedure to expose this site on the bone 50.

The operator actuates the powered drill 60 so that the cylindrical drill bit 12 is rotated so as to cut into the bone 50 around the exterior surface of the screw or pin 32. The operator selects the direction of rotation to match the direction that the screw would need to be rotated to loosen the screw from the bone and withdraw the screw from the bone. This direction is the same direction in which the cutting surface of the drill bit is configured to cut. The operator continues to rotate the cylindrical bit 12 at least until galling between the surface 22 of the cavity 20 and the exterior surface of the screw or pin 32 causes the screw or pin to adhere to the interior surface 22 of the cavity wall 34 of the drill bit 12. FIG. 2 illustrates a typical case in which screw 32, which has broken just beneath surface 52 of bone 50, seizes against interior surface 22 of the third section 25 of cylindrical drill bit 12. Once a bond is formed between the interior surface 22 of cavity wall 34 of the drill bit 12 and the exterior surface of the screw or pin 32, the cylindrical drill bit 12 and the adhered pin or screw 32 can be removed from the bone 50. If a threaded screw is being removed, as the operator rotates the drill bit in the direction that unscrews the screw, the screw will move away from and out of the bone. If an unthreaded pin is being removed, once the pin becomes fixed to the interior surface 22 of the cavity 20 in the drill bit 12, the operator then can move the cylindrical drill bit away from the bone 50 and remove the adhered pin. The removed fastening implement, be it pin or screw, then can be discarded together with the drill bit to which the implement has become adhered. Moreover, as shown in FIG. 2 for example, the drill bit 12 it rotated so as to move the drilling debris 54 toward the central axis 30 and into the spaces between the threads of the screw as well as into cavity 20 of the cylindrical drill bit 12.

In many applications, the screws or pins become adhered to the bone by a condition known as osteoclasis or osteo-metallic bonding, whereby bonding material forms at the interface of the screw and the surrounding bone to lock the exterior surface of the screw to the bone. This bonding material that develops between the screw and the bone, prevents new bone growth. However, in using the device of the present invention, the material that bonds the screw to the bone becomes removed before the exterior surface of the screw contacts the interior surface 22 of cavity 20 of the removal device. Moreover, once the screw or pin is removed by the present invention, the section of bone containing the bonding material also is removed in a manner that stimulates blood circulation and permits new bone growth to fill the hole that has been left by the removal of the screw or pin.

While a preferred embodiment of the invention has been described using specific terms, such description is for illustrative purposes only, and it is to be understood that changes and variations may be made without departing from the spirit or scope of the following claims.

What is claimed is:

1. A device for removing from bone, fastening implements embedded in the bone, the device comprising:

an elongated cylindrical member defining a proximal end and a distal end disposed generally opposite from said proximal end;

said cylindrical member defining a cavity disposed internally of said cylindrical member and having a central axis extending along the length of said cylindrical member;

said distal end defining an opening concentrically disposed with respect to said cavity and communicating with said cavity;

said distal end further defining at least one cutting surface disposed about said opening, said cutting surface being defined by a plurality of teeth; and wherein said cavity defines an interior surface having a decreasing diameter as one proceeds from said distal end to said proximal end.

2. A device as in claim 1, wherein said cavity is defined by at least two adjacent and concentric sections, each section being defined by a different diameter such that as between each two adjacent sections the diameter of the section disposed closer to said opening is the larger diameter of each said two adjacent sections and wherein at least one of said sections has a diameter sized so that as said cutting surface is rotated about said central axis of said opening, said at least one section becomes adhered to the fastening implement intended to be removed.

3. A device as in claim 2, wherein said adhered section is formed of stainless steel.

4. A device as in claim 3, wherein said cutting surface is formed of hardened stainless steel.

5. A device as in claim 1, wherein said cutting surface being configured to cut when said cutting surface is rotated about said central axis of said opening in counterclockwise direction that is the direction for unscrewing the fastening implement intended to be removed.

6. A device as in claim 1, wherein said cutting surface is formed of hardened stainless steel.

7. A device as in claim 1, further comprising a mechanism for gripping said cylindrical member and rotating said cylindrical member about said central axis of said opening.

8. A device as in claim 1, wherein said cutting surface being further configured to move debris toward said central axis of said opening.

9. A device as in claim 1, wherein said cutting surface is formed by a plurality of triangular teeth.

10. A device as in claim 9, wherein said cutting surface defines at least a first tooth, a second tooth and a third tooth, and wherein each of said three teeth defines a vertex that is circumferentially separated from the vertex of each other tooth, and wherein said circumferential separation between said vertex of said first tooth and said vertex of said second tooth differs from said circumferential separation between said vertex of said second tooth and said vertex of said third tooth.

11. A device as in claim 1, wherein said cutting surface being configured to cut when said cutting surface is rotated about said central axis of said opening in a clockwise direction that is the direction for unscrewing the fastening implement intended to be removed.

12. A device for removing from bone, fastening implements embedded in the bone, the device comprising:
- an elongated cylindrical member defining a proximal end and a distal end disposed generally opposite from said proximal end;
- said distal end defining an opening having a central axis along the length of said cylindrical member;
- an elongated cavity extending axially from said opening toward said proximal end and disposed concentrically relative to said opening;
- said cavity being defined by at least two adjacent and concentric sections, each said section being defined by a different diameter wherein as between each two adjacent sections the diameter of the section disposed closer to said opening is the larger diameter of each said two adjacent sections;
- said distal end further defining at least one cutting surface disposed about said opening, said cutting surface being defined by a plurality of teeth; and
- said cutting surface being configured to move cutting debris toward said central axis of said opening and into said cavity.

13. A method for removing from bone, fastening implements such as bone pins and headless bone screws, embedded in the bone, the method comprising the steps of:
- disposing a cylindrical drill bit having an opening configured to receive the end of the fastening implement therein and having a cavity configured with a decreasing diameter as one proceeds deeper into said cavity, concentrically around the site of the bone containing the fastening implement to be removed;
- rotating the cylindrical bit so as to cut into the bone around the exterior surface of the fastening implement at least until galling between the interior surface of the cavity and the exterior surface of the fastening implement causes the implement to adhere to the interior surface of the cavity of the drill bit; and
- withdrawing the cylindrical drill bit and adhered implement from the bone.

14. A method as in claim 13, further comprising the step of rotating the cylindrical bit in a direction that is the direction for unscrewing the fastening implement intended to be removed.

15. A method as in claim 13, further comprising the step of rotating the drill bit so as to move drilling debris toward the central axis and into the cavity of the cylindrical drill bit.

* * * * *